United States Patent [19]

Franckowiak et al.

[11] Patent Number: 5,008,279

[45] Date of Patent: Apr. 16, 1991

[54] CIRCULATION-ACTIVE FLUOROMETHOXYPHENYL DIHYDROPYRIDINE COMPOUNDS

[75] Inventors: Gerhard Franckowiak, Wuppertal; Jürgen Stoltefuss, Haan; Martin Bechem; Rainer Gross, both of Wuppertal; Michael Kayser, Leverkusen; Siegbert Hebisch, Oberhausen; Matthias Schramm, Cologne, all of Fed. Rep. of Germany

[73] Assignee: Bayer Aktiengesellschaft, Leverkusen, Fed. Rep. of Germany

[21] Appl. No.: 263,671

[22] Filed: Oct. 27, 1988

[30] Foreign Application Priority Data

Nov. 4, 1987 [DE] Fed. Rep. of Germany ....... 3737340

[51] Int. Cl.$^5$ ............... C07D 211/90; C07D 401/12; A61K 31/44
[52] U.S. Cl. ............................ 514/354; 514/332; 514/318; 514/257; 546/208; 546/256; 546/322; 544/333; 544/266
[58] Field of Search ............... 546/208, 256, 322; 544/333, 266; 514/332, 318, 257, 354

[56] References Cited

U.S. PATENT DOCUMENTS 4,285,955  8/1981  Wehinger et al. ............... 546/322
4,764,516  8/1988  Franckowiak et al. .......... 514/256

FOREIGN PATENT DOCUMENTS 0186028  7/1986  European Pat. Off. .......... 546/322

OTHER PUBLICATIONS

Chemical Abstracts, vol. 103, No. 9, Abstract 64628p, Sep. 2, 1985, pp. 64628–64629.
Chemical Abstracts, vol. 105, No. 19, Abstract, Nov. 10, 1986, p. 172305.
Schramm et al., *Nature*, vol. 303, Jun. 9, 1983, pp. 535–537.

*Primary Examiner*—Mary C. Lee
*Assistant Examiner*—Zinna Northington-Davis

*Attorney, Agent, or Firm*—Sprung Horn Kramer & Woods

[57] ABSTRACT

Circulation-active fluoromethoxyphenyldihydropyridines of the formula

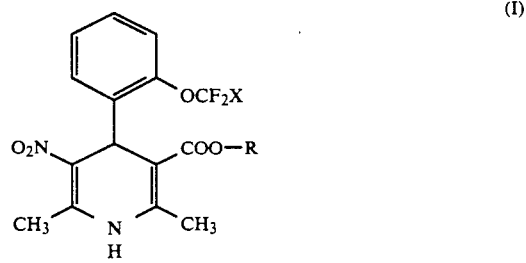

in which
  X stands for hydrogen or fluorine and
  R stands for straight-chain, branched or cyclic alkyl or alkenyl having 2 to 12 carbon atoms which can be interrupted by 1 to 2 oxygen and/or sulphur atoms in the chain, and which can be monosubstituted or polysubstituted
  (a) by hydroxyl, aryl having 6 to 12 carbon atoms, aryloxy having 6 to 12 carbon atoms, where the aryl radical is again substituted by alkyl having up to 4 carbon atoms, alkoxy having up to 4 carbon atoms or halogen, the substituents being identical or different, or
  (b) by carboxyl, alkoxycarbonyl having up to 6 carbon atoms, pyridyl, piperidyl, pyrimidyl, acyloxy having up to 7 carbon atoms, sulphamoyl, carbamoyl, halogen or cyano, the substituents being identical or different, or
  (c) by an amino group, where the amino group can carry one or two identical or different substituents from the group consisting of alkyl having up to 6 carbon atoms, benzyl, phenyl or acyl having up to 7 carbon atoms,
and salts thereof.

15 Claims, No Drawings

CIRCULATION-ACTIVE FLUOROMETHOXYPHENYL DIHYDROPYRIDINE COMPOUNDS

The present invention relates to new fluoromethoxyphenyl dihydropyridines, several processes for their preparation and their use in medicaments, in particular in circulation-influencing agents having positive inotropic action.

It has already been disclosed that 1,4-dihydropyridines possess blood vessel-dilating properties and can be used as coronary agents and antihypertensives (compare Brit. Patent 1,173,062 and 1,358,951; DE-OS (German Published Specification) 2,629,892 and 2,752,820). Furthermore, it is known that 1,4-dihydropyridines cause an inhibition of the contractility of smooth and cardiac muscles and can be employed for the treatment of coronary and blood vessel diseases (compare Fleckenstein, Ann. Rev. Pharmcol. Toxicol. 17, 149–166 (1977)).

With knowledge of these properties of the dihydropyridines, it was not foreseeable that the compounds according to the invention would possess a positive inotropic action increasing the contractile force on the heart muscle.

The invention relates to new fluoromethoxyphenyl dihydropyridines of the general formula (I)

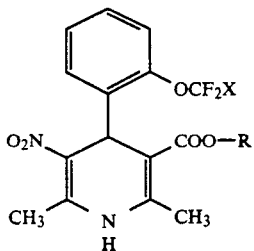

(I)

in which

X stands for hydrogen or fluorine and

R stands for straight-chain, branched or cyclic alkyl or alkenyl having 2 to 12 carbon atoms which can be interrupted by 1 to 2 oxygen and/or sulphur atoms in the chain, and which can be monosubstituted or polysubstituted (a) by hydroxyl, aryl having 6 to 12 carbon atoms, aryloxy having 6 to 12 carbon atoms, where the aryl radical is again substituted by alkyl having up to 4 carbon atoms, alkoxy having up to 4 carbon atoms or halogen, the substituents being identical or different, or (b) by carboxyl, alkoxycarbonyl having up to 6 carbon atoms, pyridyl, piperidyl, pyrimidyl, acyloxy having up to 7 carbon atoms, sulphamoyl, carbamoyl, halogen or cyano, the substituents being identical or different, or (c) by an amino group, where the amino group can carry one or two identical or different substituents from the series comprising alkyl having up to 6 carbon atoms, benzyl, phenyl or acyl having up to 7 carbon atoms, in the form of racemates and optically pure forms and their salts.

Preferred compounds of the general formula (I) are those in which

X stands for hydrogen or fluorine, and

R stands for straight-chain, branched or cyclic alkyl having 2 to 12 carbon atoms, which can be interrupted by oxygen and/or sulphur in the chain, and which can be monosubstituted or disubstituted by hydroxyl, cyano, phenyl, by phenoxy which is optionally substituted by methoxy, methyl, fluorine or chlorine, by alkoxycarbonyl having up to 6 carbon atoms, by pyridyl, piperidyl, acetoxy, benzoyloxy or by an amino group, where the amino group can carry one or two identical or different substituents from the series comprising alkyl having up to 4 carbon atoms or benzyl, or for straight-chain or branched alkenyl having up to 10 carbon atoms, the substituents being identical or different, and their salts Particularly preferably, compounds of the general formula (I) may be mentioned, in which X stands for hydrogen or fluorine, and R stands for straight-chain or branched alkyl having 2 to 12 carbon atoms which can be interrupted by an oxygen atom or a sulphur atom in the chain and which can be monosubstituted or disubstituted by hydroxyl, cyano, phenyl, phenoxy, 4-methoxyphenoxy, pyridyl, alkoxycarbonyl having up to 4 carbon atoms, amino or benzylmethylamino, the substituents being identical or different, or for straight-chain or branched alkenyl having up to 10 carbon atoms, or for cyclopropyl, cyclopentyl, cyclohexyl, cyclopropylmethyl, cyclopentylmethyl or cyclohexylmethyl, and their salts.

Physiologically acceptable salts may be salts of the compounds according to the invention with inorganic or organic acids. Examples which may be mentioned are: hydrohalides such as, for example, hydrochlorides or hydrobromides, hydrogen sulphates, sulphates, hydrogen phosphates, phosphates, or acetates, maleates, fumarates, citrates, tartrates, lactates or benzoates.

The compounds of the formula (I) according to the invention, in which

R has the abovementioned meaning, are obtained by reacting

[A] aldehydes of the formula (II)

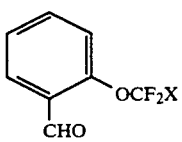

(II)

in which

X has the abovementioned meaning, and nitroacetone of the formula (III)

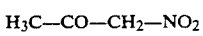

(III)

or their Knoevenagel condensation product of the formula (IV)

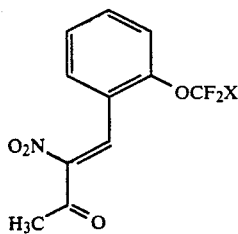 (IV)

in which

X has the abovementioned meaning, and aminocrotonic acid esters of the general formula (V)

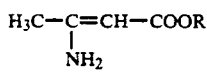 (V)

in which

R has the abovementioned meaning, if appropriate in the presence of an inert solvent, or

[B] the dihydropyridine derivative of the formula (VI)

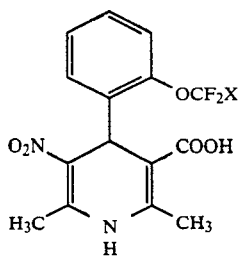 (VI)

which

X has the abovementioned meaning, with alcohols of the formula (VII)

R—OH (VII)

in which

R has the abovementioned meaning, according to known methods, if appropriate via a reactive acid derivative, or

[C] aldehydes of the formula (II) and acetoacetic acid ester of the formula (VIII)

H$_3$C—CO—CH$_2$—COOR (VIII)

or their Knoevenagel condensation products of the formula (IX)

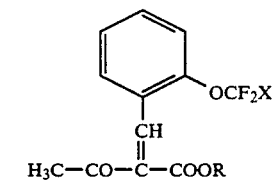 (IX)

in which

X and R have the abovementioned meanings, with nitroacetone and ammonium salts such as, for example, ammonium acetate, if appropriate in the presence of an inert solvent, and if appropriate converting the dihydropyridines obtained into their optically active isomers by customary methods.

Pure enantiomeric forms are obtained, for example, by resolving diastereomer mixtures of dihydropyridines of the formula (X)

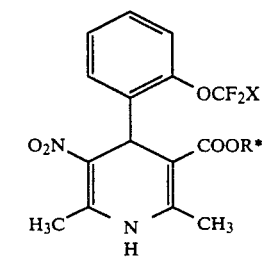 (X)

in which

X has the abovementioned meaning, and

R* represents an optically active ester radical, into the individual diastereomers by crystallization, chromatography or Craig partition, subsequently preparing the pure enantiomeric carboxylic acids of the formula XI

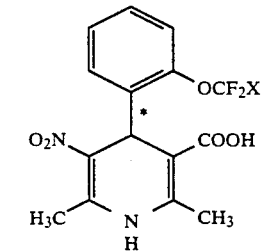 (XI)

and then reacting these, if appropriate by esterification with alcohols of the general formula (VII), to give the corresponding pure enantiomeric dihydropyridines of the formula (I).

According to the type of starting material used, the synthesis of the racemic compounds by processes A to C can be illustrated by the following equations:

[A]

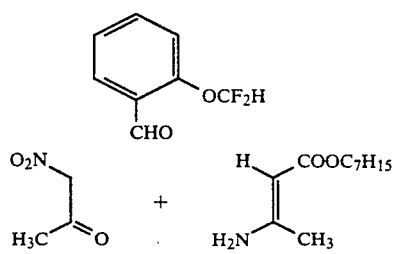

or 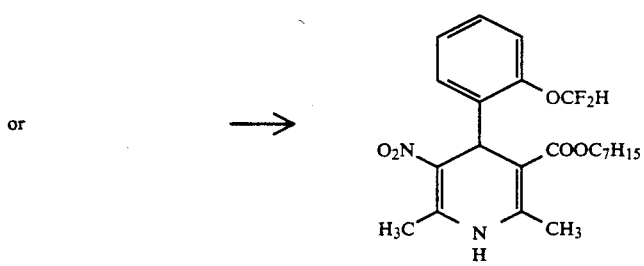
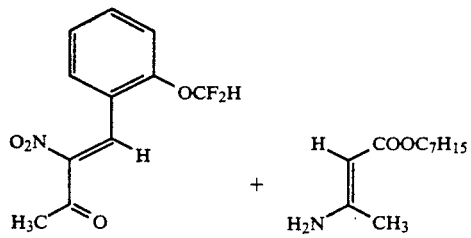
[B]
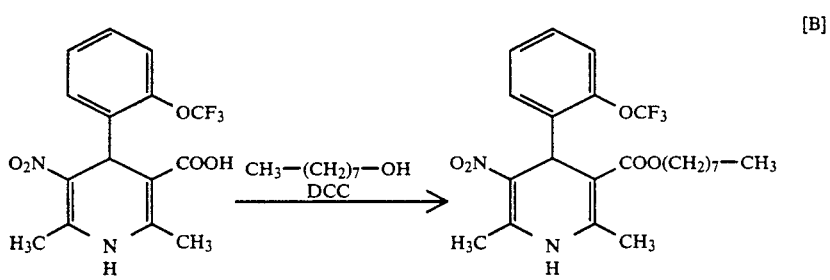
[C]
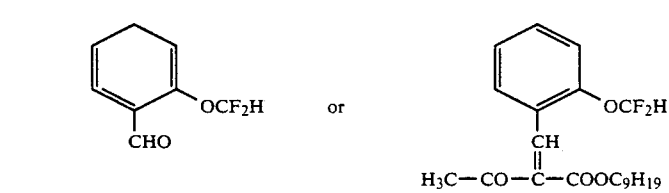
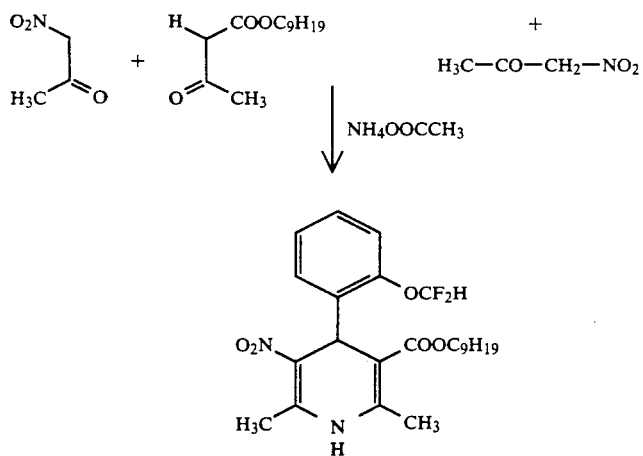
The resolution of enantiomers can be illustrated, or example, by the following equation:

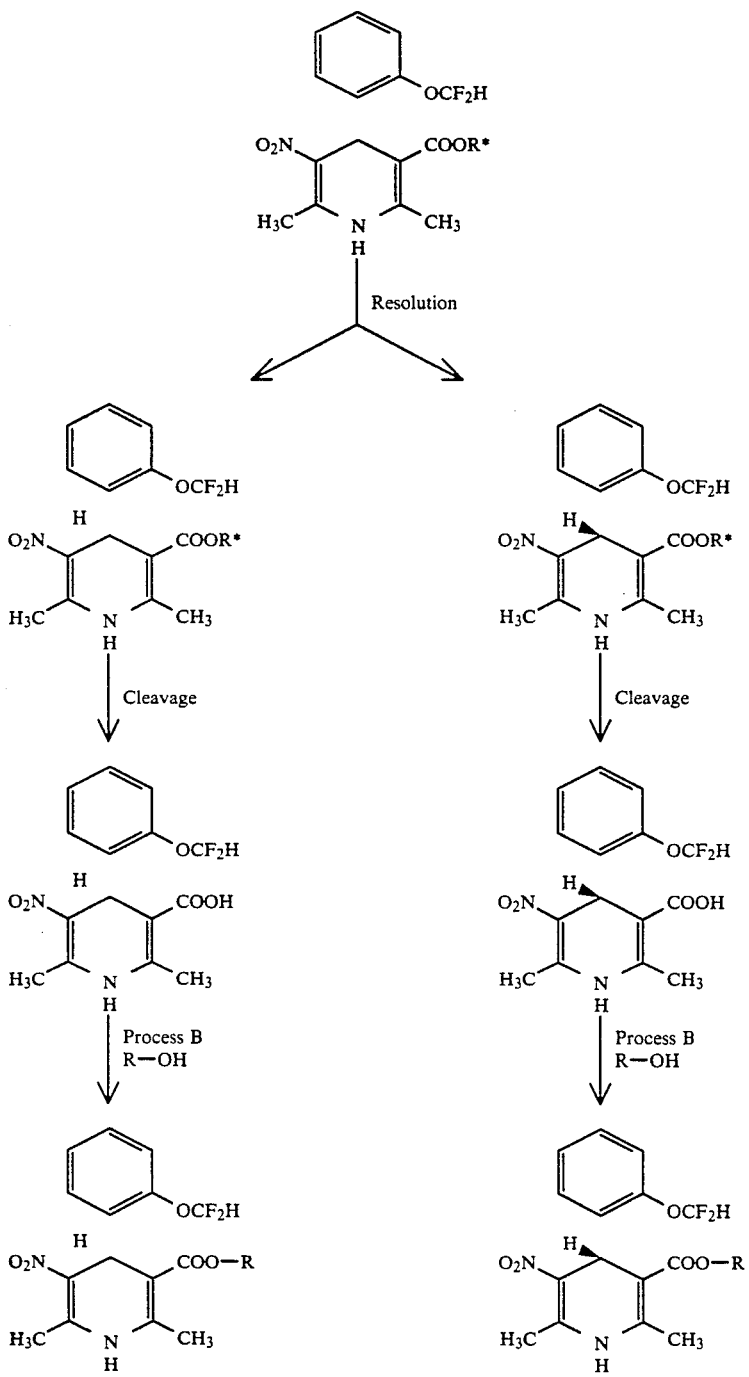

The compounds according to the invention exist in stereoisomeric forms which behave either as image and mirror image (enantiomers) or not as image and mirror image (diastereomers). The invention relates both to the antipodes and to the racemic forms and also the diastereomer mixtures. The racemic forms can be resolved into the stereoisomerically homogeneous constituents in a known manner, just like the diastereomers (compare E. L. Eliel, Stereochemistry of Carbon Compounds, McGraw Hill, 1962).

Suitable chiral ester radicals are all esters of pure enantiomeric alcohols such as, for example, 2-butanol, 1-phenylethanol, lactic acid, lactic acid esters, mandelic acid, mandelic acid esters, 2-aminoalcohols, sugar derivatives and many other pure enantiomeric alcohols.

The resolution of the diastereomers in general takes place either by fractional crystallization, by column chromatography or by Craig partition. Which is the optimum method must be decided from case to case, sometimes it is also expedient to use combinations of the individual methods. Resolution by crystallization or Craig partition or a combination of both methods is particularly suitable.

Solvents used are the solvents customary for such procedures preferably such as alcohols such as methanol, ethanol, n- or iso-propanol, ethers such as diethyl ether, tetrahydrofuran, dioxane or glycol monomethyl ether or glycol diethyl ether, glacial acetic acid, pyridine, dimethylformamide, dimethyl sulphoxide, acetonitrile, hexamethylphosphoric triamide, toluene, acetone, methylene chloride, hexane, formamide, water, ethyl acetate, etc.

The removal of the chiral ester groups can, according to the type of chiral ester, take place by acidic or alkaline hydrolysis or by $\beta$-elimination in the solvents customary for such procedures.

The temperatures can be varied within a wide range. Preferred temperatures are between 20° C. and 100° C.

The esterification of the pure enantiomeric dihydropyridine carboxylic acids of the formula XI with the alcohols of the formula VII to give the pure enantiomeric compounds of the formula I takes place by known methods, if appropriate via a reactive acid derivative by the customary methods for esterification in the customary solvents, preferably such as ethers such as diethyl ether or tetrahydrofuran, dimethylformamide, methylene chloride, chloroform, acetonitrile, toluene etc.

Preferred temperatures for esterification are temperatures between 0° C. and 100° C.

Moreover, it is possible to obtain the pure enantiomeric carboxylic acids by resolution of the racemic carboxylic acids and then to react these, as described in process B, with alcohols of the formula VII.

The fluoromethoxybenzaldehydes used as starting materials can be prepared from salicylaldehyde by methods customary in fluorine chemistry.

Nitroacetone (III) is known [N. Levy and C. W. Scaife, J. Chem. Soc. (London) 1946, 1100, C. D. Hurd and M. E. Nilson, J. Org. Chem. 20, 927 (1955)].

The ylidene compounds IV are new, but can be prepared by known methods (compare H. Dornow and W. Sassenberg, Liebigs Ann. Chem. 602, 14 (1957)).

The aminocrotonates of the formula V are known or can be prepared by known methods [S. A. Glickman and A. C. Cope, J. Am. Chem. Soc. 67, 1017 (1945)].

The acetoacetates of the formula VIII according to the invention are known or can be prepared by known methods [compare D. Borrmann, "Umsetzung von Diketen mit Alkoholen, Phenolen und Mercaptanen" ("Reaction of diketene with alcohols, phenols and mercaptans"), in Houben-Weyl, Methoden der organischen Chemie (Methods of Organic Chemistry), Vol. VII/4, 230 ff (1968)].

The ylidene compounds of the formula IX utilizable according to the invention are known or can be prepared by known methods [Organic Reactions XV, 204 ff (1967)].

The racemic DHP carboxylic acids VI are new, but can be prepared by known methods [compare EP-71,819].

The compounds of the formula I, in which R stands for a chiral radical, can be prepared by processes A to C.

Suitable diluents for processes A to C are all inert organic solvents. These preferably include alcohols such as methanol, ethanol, n- or iso-propanol, butanol, ethers such as diethyl ether, tetrahydrofuran, dioxane or glycol monoethyl ether or glycol diethyl ether, glacial acetic acid, pyridine, dimethylformamide, dimethyl sulphoxide, acetonitrile, hexamethylphosphoric triamide or toluene.

The reaction temperatures for processes A to C can be varied within a relatively wide range. In general, the reaction is carried out in a range from 10° C. to 200° C., preferably from 20° C. to 150° C.

When carrying out the process according to the invention, the ratio of the substances taking part in the reaction is arbitrary. In general, however, the reaction is carried out using molar amounts of the reactants.

The preceding preparation processes are only given for illustration. The preparation of the compounds of the formula (I) is not limited to these processes, but any modification to these processes is utilizable in a similar manner for the preparation of the compounds according to the invention.

The compounds according to the invention show an unforeseeable, valuable spectrum of pharmacological action. They influence the contractile force of the heart and the smooth muscle tone. They can therefore be employed in medicaments for influencing pathologically altered blood pressure, as coronary therapeutics and for the treatment of cardiac insufficiency. Moreover, they can be used for the treatment of cardiac arrhythmias, for lowering blood sugar, for detumescing mucous membranes and for influencing the salt and liquid balance.

Some of the short-chain alkyl esters of the compounds according to the invention (in particular those having $R < C_6$) show a very strong positive inotropic action, which may, however, simultaneously be combined with a blood vessel-constricting action.

The cardiac and blood vessel actions were discovered on isolated perfused guineapig hearts. For this, the hearts of 250 to 350 g weight guineapigs are used. The animals are killed by a blow to the head, the thorax is opened, and a metal cannula is tied into the exposed aorta. The heart is separated out from the thorax with the lungs and is connected to the perfusion apparatus for continuous perfusion via an aortic cannula. The lungs are separated from the roots of the lung. A Krebs-Henseleit solution (1) (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$ and 0.013 mmol/l of $Na_2EDTA$), whose $CaCl_2$ content is 1.2 mmol/l, is used as the perfusion medium. 10 mmol/l of glucose is used as energy-producing substrate. The solution is filtered free from particles before the perfusion. The solution is aerated using a 95% $O_2$, 5% $CO_2$ mixture to maintain a pH of 7.4. The hearts are perfused using a constant flow (10 ml/min) at 32° C. by means of a peristaltic pump.

For measurement of the cardiac function, a liquid-filled latex balloon, which is connected with a pressure transducer via a liquid column, is introduced into the left ventricle through the left auricle, and the isovolumetric contractions are recorded on a rapid recorder (Opie, L., J. Physiol. 180 (1965), 529–541). The perfusion pressure is recorded by means of a pressure transducer which is connected with the perfusion system before the heart. Under these conditions, a decrease of the perfusion pressure indicates a coronary dilatation, and an increase or decrease of the left ventricular contraction amplitude indicates a decrease or an increase in cardiac contractility. The compounds according to the invention are perfused into the perfusion system in suitable dilutions shortly before the isolated heart.

The new active compounds may be converted in a customary manner into the customary formulations, such as tablets, dragees, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient to achieve the dosage range indicated.

The formulations are prepared, for example, by extending the active compound using solvents and/or excipients, if appropriate using emulsifiers and/or dispersants, where, for example, in the case of the use of water as a diluent, organic solvents can be used, if appropriate, as auxiliary solvents.

Auxiliaries which may be mentioned, for example, are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, aluminas, talc, chalk), ground synthetic minerals (for example highly disperse silica, silicates), sugars (for example sucrose, lactose and dextrose), emulsifiers (for example polyoxyethylene fatty acid esters, polyxoyethylene fatty alcohol ethers, alkylsulphonates and arylsulphonates), dispersants (for example lignin-sulphite waste liquors, methylcellulose, starch and polyvinylpyrrolidone) and lubricants (for example magnesium stearate, talc, stearic acid and sodium lauryl sulphate).

Administration takes place in a customary manner, preferably orally or parenterally, in particular perlingually or intravenously. In the case of oral administration, tablets can of course also contain additives, such as sodium citrate, calcium carbonate and dicalcium phosphate together with various additives, such as starch, preferably potato starch, gelatine and the like in addition to the excipients mentioned. Furthermore, lubricants such as magnesium stearate, sodium lauryl sulphate and talc may be used for the preparation of tablets. In the case of aqueous suspensions, various flavor - improvers or colorants can be added to the active compound in addition to the excipients mentioned.

In the case of parenteral use, solutions of the active compound using suitable liquid excipients can be employed.

In general, it has proved advantageous with intravenous administration to administer amounts of about 0.001 to 1 mg/kg, preferably about 0.01 to 0.5 mg/kg of body weight to achieve effective results, and with oral administration the dosage is about 0.01 to 20 mg/kg, preferably 0.1 to 10 mg/kg of body weight.

In spite of this, it may be necessary to deviate from the amounts mentioned, depending upon the body weight or the type of administration route, individual behaviour towards the medicament, the type of its formulation and the point in time or interval at which administration takes place. Thus, in some cases it may be sufficient to manage with less than the previously mentioned minimum amount, whereas in other cases the upper limit mentioned must be exceeded. In the case of administration of larger amounts, it may be advisable to divide these into several individual doses over the day.

EXPERIMENTAL PART

EXAMPLE 1

3-Phenylpropyl 4-(2-difluoromethoxyphenyl)-1,4-dihydro-2,6-dimethyl-3-nitropyridine-5-carboxylate

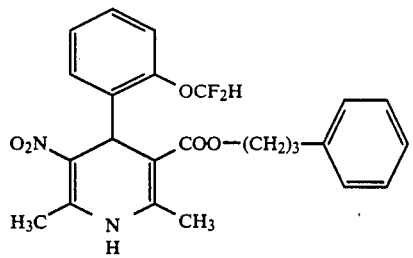

Process variation A 3.4 g (20 mmol) of 2-difluoromethoxybenzaldehyde in 30 ml of ethanol are boiled for 4 hours with 3.6 g (35 mmol) of nitroacetone, 4.4 g (20 mmol) of 3-phenylpropyl β-aminocrotonate and 1.2 ml (20 mmol) of acetic acid. The mixture is cooled and concentrated. The oily evaporation residue is dissolved in ethyl acetate, washed with water, sodium hydrogen carbonate solution and water again, dried and concentrated. The oily crude product obtained is purified over a silica gel column of 360 ml volume using toluene/ethyl acetate. The oil obtained crystallizes on stirring with ether. The crystals are filtered off with suction and washed with ether. 2.2 g (24% of theory) of yellow crystals of melting point 162°–164° C. are obtained.

EXAMPLE 2 n-Butyl 4-(2-difluoromethoxyphenyl)-1,4-dihydro-2,6-dimethyl-3-nitropyridine-5-carboxylate

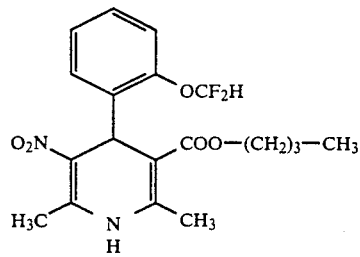

Process variation A 3.86 g (15 mmol) of 2-difluoromethoxybenzylidenenitroacetone in 25 ml of ethanol are boiled for 4 hours with 2.4 g (15 mmol) of butyl 8-aminocrotonate and 0.9 ml (15 mmol) of acetic acid. The mixture is cooled and concentrated. The oily evaporation residue is taken up in ethyl acetate, washed with water, sodium hydrogen carbonate solution and water again, dried and concentrated. The oily residue crystallizes under hexane after the addition of a little ether. The crystals are filtered off with suction and washed with hexane/ether in a volume ratio of 10:1. 5.1 g (85.9% of theory) of orange-yellow crystals of melting point 118°–120° C. are obtained.

EXAMPLE 3

Preparation of pure enantiomers via chiral esters

1(S)-(1-Isopropoxycarbonylethyl) 4-(2-difluoromethoxyphenyl)-1,4-dihydro-2,6-dimethyl-3-nitropyridine-5-carboxylate

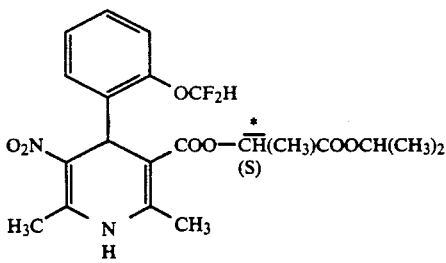

5.14 g (20 mmol) of 2-difluoromethoxybenzylidenenitroacetone in 25 ml of ethanol are boiled for 4 hours with 4.3 g (20 mmol) of 1(S)-(1-isopropoxycarbonylethyl) β-aminocrotonate and 1.2 ml (20 mmol) of glacial acetic acid. The mixture is concentrated, dissolved in ethyl acetate and washed with water, sodium hydrogen carbonate solution and water again, dried and evaporated. The evaporation residue obtained is dissolved in a little ether and allowed to stand, as a result of which one diastereomer crystallizes out. It is filtered off with suction and washed with ether. 2.13 g (23.5%) of yellow-colored crystals of melting point 167°–169° C. are obtained.

EXAMPLE 4

4-(2-Difluoromethoxyphenyl)-1,4-dihydro-2,6-dimethyl-3-nitropyridine-5-carboxylic acid ((−)-enantiomer)

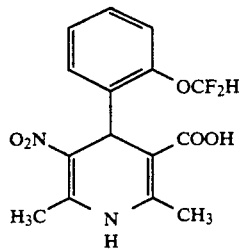

1.14 g (2.5 mmol) of the crystals obtained according to Example 3 in 40 ml of dioxane and 50 ml of 1.5N sodium hydroxide solution are stirred for 48 hours. The mixture is concentrated somewhat and extracted by shaking 2× with methylene chloride. The aqueous phase is acidified using 10% strength hydrochloric acid, extracted by shaking 2× with ethyl acetate, washed with water, dried and concentrated. The product was purified over a short silica gel column. 245 mg (28.8%) of yellow-colored foam are obtained having a rotation $[\alpha]_{589}^{20} = -17.6$ (c=0.512, acetone).

EXAMPLE 5

Analogously to Example 4, (+)-4-(2-difluoromethoxyphenoxy)-1,4-dihydro-2,6-dimethyl-3-nitropyridine-5-carboxylic acid is obtained from the other diastereomer $[\alpha]_{589}^{20} = +20.4$ (c=1.023 acetone)

EXAMPLE 6

Process variation B
6-Hydroxyhexyl 4-(2-difluoromethoxyphenyl)-1,4-dihydro-2,6-dimethyl-3-nitropyridine-5-carboxylate ((−)-enantiomer)

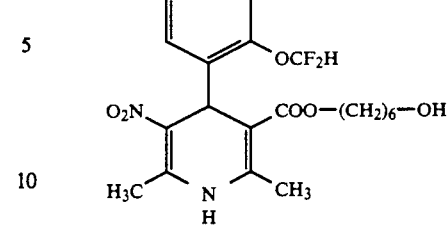

1.5 g (4.4 mmol) of the compound from Example 5 are dissolved in 10 ml of absolute dimethylformamide and stirred successively with 10 g of 1,6-hexanediol, 0.44 g of 4-dimethylaminopyridine and 2.55 g (6 mmol) of 1-cyclohexyl-3-(2-morpholinoethyl)-carbodiimide-p-methoxytoluenesulphonate for 44 hours. The mixture is filtered off from precipitated salt with suction, the filtrate is concentrated, and the oily residue is taken up in ethyl acetate, washed with water, about 5% strength hydrochloric acid, water, sodium hydrogen carbonate solution and water again, dried and concentrated. The evaporation residue is purified by flash chromatography using cyclohexane/toluene mixtures. The pure fractions are concentrated, crystallized by stirring with ether, filtered off with suction and washed with ether. 1.4 g (72% of theory) of yellow crystals of melting point 122°–124° C. are obtained.

$[\alpha]_{589}^{20} = -24.64$ (c=0.9365, chloroform)

The following were prepared analogously to Example 1 to 3:

EXAMPLE 7

Ethyl 4-(2-difluoromethoxyphenyl)-1,4-dihydro-2,6-dimethyl-3-nitropyridine-5-carboxylate

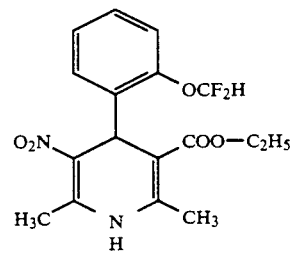

Melting point: 92° C.

EXAMPLE 8

Isopropyl 4-(2-difluoromethoxyphenyl)-1,4-dihydro-2,6-dimethyl-3-nitropyridine-5-carboxylate

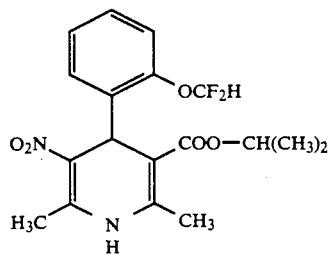

Melting point: resin

EXAMPLE 9

β-Cyanoethyl 4-(2-difluoromethoxyphenyl)-1,4-dihydro-2,6-dimethyl-3-nitropyridines-5-carboxylate

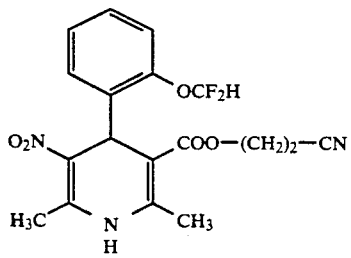

Melting point: 150° C.

EXAMPLE 10

3,3-Dimethylbutyl 4-(2-difluoromethoxyphenyl)-1,4-dihydro-2,6-dimethyl-3-nitropyridine-5-carboxylate

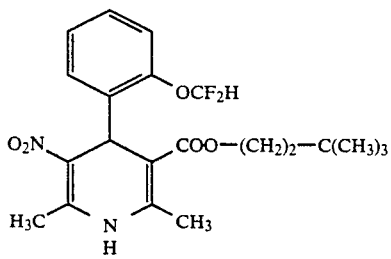

Melting point: resin

EXAMPLE 11

2-Aceteoxyethyl 4-(2-difluoromethoxyphenyl)-1,4-dihydro-2,6-dimethyl-3-nitropyridine-5-carboxylate

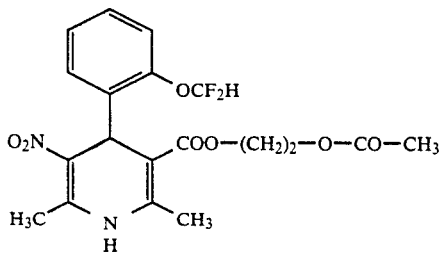

Melting point: 137° C.

EXAMPLE 12

2-N-Piperidinylethyl 4-(2-difluoromethoxyphenyl)-1,4-dihydro-2,6-dimethyl-3-nitropyridine-5-carboxylate

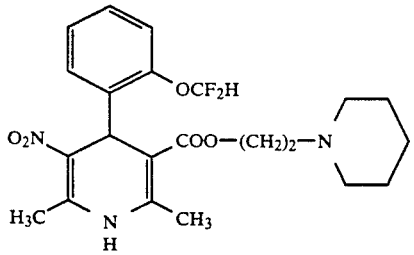

Melting point: resin

EXAMPLE 13

2-(N-Benzyl-N-methyl)aminoethyl 4-(2-difluoromethoxyphenyl)-1,4-dihydro-3-nitropyridine-5-carboxylate

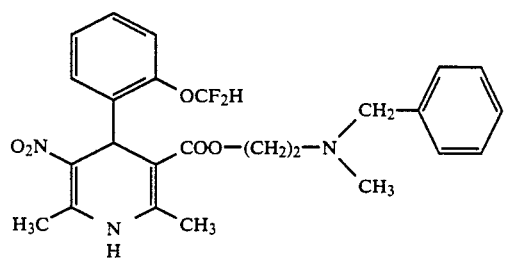

Melting point: resin

EXAMPLE 14

2-(2-Pyridyl)ethyl 4-(2-difluoromethoxyphenyl)-1,4-dihydro-2,6-dimethyl-3-nitropyridine-5-carboxylate

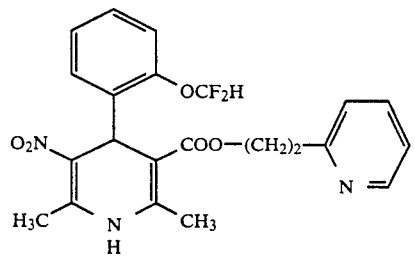

Melting point: 159° C.

EXAMPLE 15

Octyl 4-(2-difluoromethoxyphenyl)-1,4-dihydro-2,6-dimethyl-3-nitropyridine-5-carboxylate

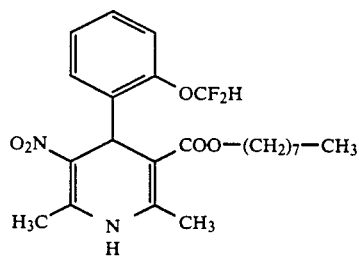

Melting point: 99°–100° C.

EXAMPLE 16

2-(4-Methoxyphenyloxy)ethyl 4-(2-difluoromethoxyphenyl)-1,4-dihydro-2,6-dimethyl-3-nitropyridine-5-carboxylate

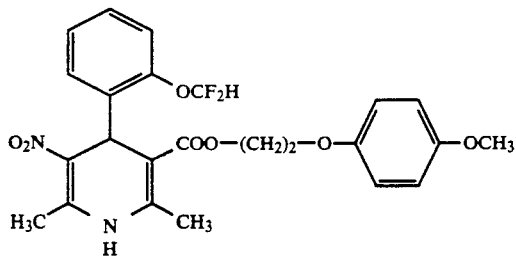

Melting point: 115°-118° C.

EXAMPLE 17

Dodecyl 4-(2-difluoromethoxyphenyl)-1,4-dihydro-2,6-dimethyl-3-nitropyridine-5-carboxylate

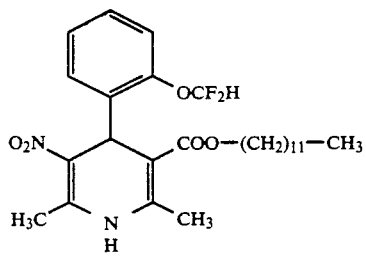

Melting point: 88°-90° C.

EXAMPLE 18

3-Phenoxypropyl 4-(2-difluoromethoxyphenyl)-1,4-dihydro-2,6-dimethyl-3-nitropyridine-5-carboxylate

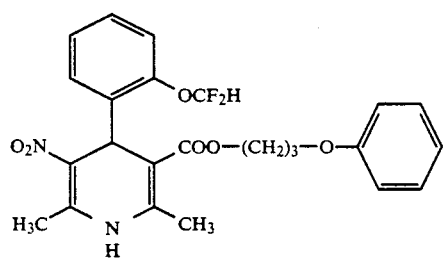

Melting point: 146°-149° C.

EXAMPLE 19

2-Phenethyl 4-(2-difluoromethoxyphenyl)-1,4-dihydro-2,6-dimethyl-3-nitropyridine-5-carboxylate

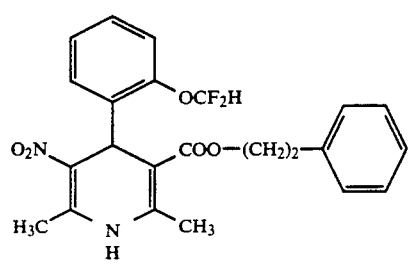

Melting point: 123° C.

EXAMPLE 20

5-Phenylpentyl 4-(2-difluoromethoxyphenyl)-1,4-dihydro-2,6-dimethyl-3-nitropyridine-5-carboxylate

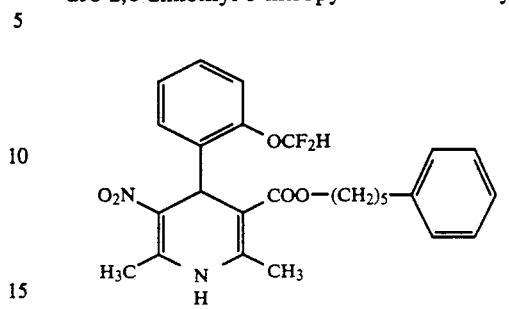

Melting point: 88°-90° C.

EXAMPLE 21

Nonyl 4-(2-difluoromethoxyphenyl)-1,4-dihydro-2,6-dimethyl-3-nitropyridine-5-carboxylate

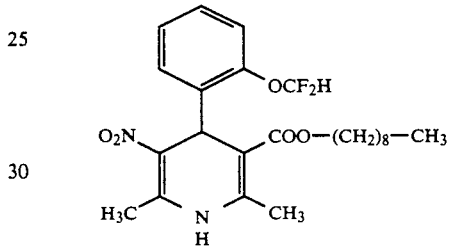

Melting point: 96°-97° C.

EXAMPLE 22

4-Phenylbutyl 4-(2-difluoromethoxyphenyl)-1,4-dihydro-2,6-dimethyl-3-nitropyridine-5-carboxylate

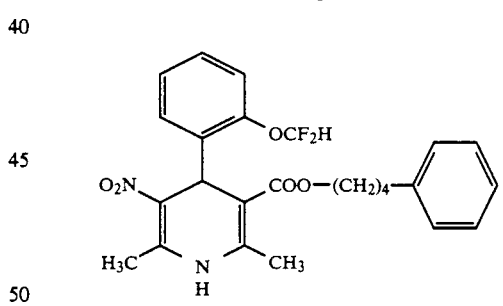

Melting point: from 106° C.

EXAMPLE 23

Heptyl 4-(2-difluoromethoxyphenyl)-1,4-dihydro-2,6-dimethyl-3-nitropyridine-5-carboxylate

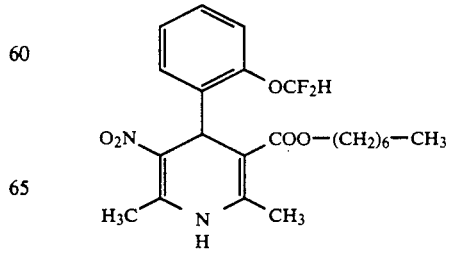

Melting point: 78°-80° C.

EXAMPLE 24

Hexyl 4-(2-difluoromethoxyphenyl)-1,4-dihydro-2,6-dimethyl-3-nitropyridine-5-carboxylate

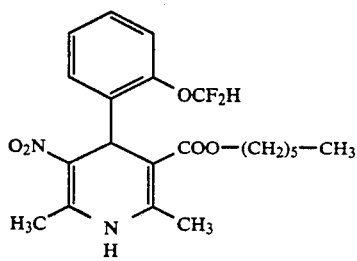

Melting point: 98°-100° C.

EXAMPLE 25

Pentyl 4-(2-difluoromethoxyphenyl)-1,4-dihydro-2,6-dimethyl-3-nitropyridine-5-carboxylate

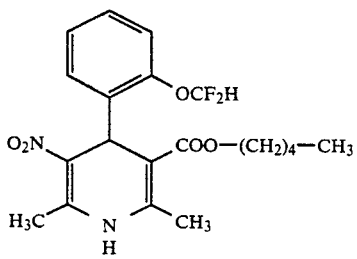

Melting point: 98°-100° C.

EXAMPLE 26

2-Heptyloxyethyl 4-(2-difluoromethoxyphenyl)-1,4-dihydro-2,6-dimethyl-3-nitropyridine-5-carboxylate

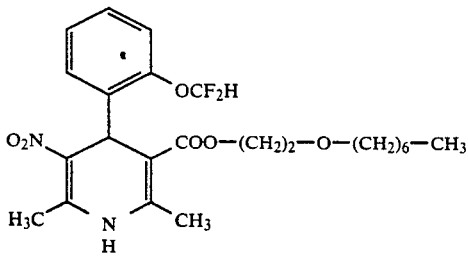

Melting point: 70°-73° C.

EXAMPLE 27

2-Hexyloxyethyl 4-(2-difluoromethoxyphenyl)-1,4-dihydro-2,6-dimethyl-3-nitropyridine-5-carboxylate

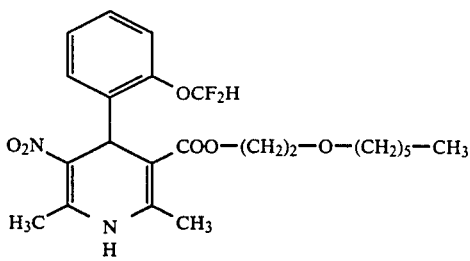

Melting point: 85° C.

EXAMPLE 28

2-Pentyloxyethyl 4-(2-difluoromethoxyphenyl)-1,4-dihydro-2,6-dimethyl-3-nitropyridine-5-carboxylate

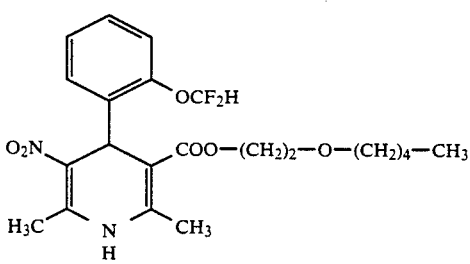

Melting point: 99°-101° C.

EXAMPLE 29

2-Butyloxyethyl 4-(2-difluoromethoxyphenyl)-1,4-dihydro-2,6-dimethyl-3-nitropyridine-5-carboxylate

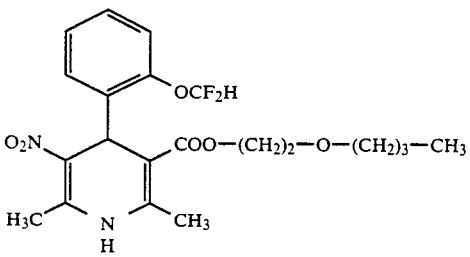

Melting point: 92°-93° C.

EXAMPLE 30

2-Ethylthioethyl 4-(2-difluoromethoxyphenyl)-1,4-dihydro-2,6-dimethyl-3-nitropyridine-5-carboxylate

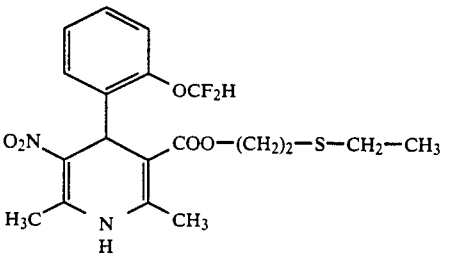

Melting point: 84°-85° C.

EXAMPLE 31

6-Hydroxyhexyl 4-(2-difluoromethoxyphenyl)-1,4-dihydro-2,6-dimethyl-3-nitropyridine-5-carboxylate

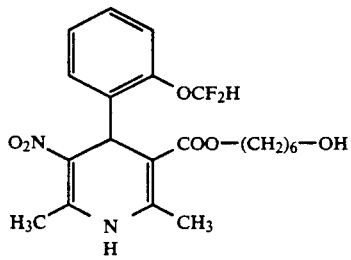

Melting point: 127° C.

EXAMPLE 32

3-Methoxycarbonylpropyl 4-(2-difluoromethoxyphenyl)-1,4-dihydro-2,6-dimethyl-3-nitropyridine-5-carboxylate

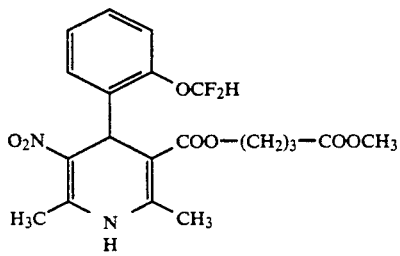

Melting point: 139°-140° C.

EXAMPLE 33

1-Ethoxycarbonylethyl 4-(2-difluoromethoxyphenyl)-1,4-dihydro-2,6-dimethyl-3-nitropyridine-5-carboxylate (diastereomer A)

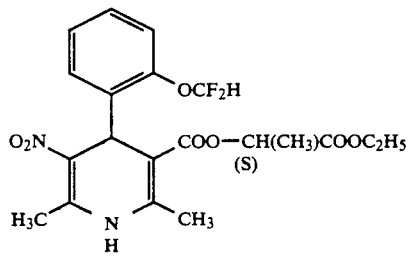

Melting point: 140°-141° C.

EXAMPLE 34

1-Ethoxycarbonylethyl 4-(2-difluoromethoxyphenyl)-1,4-dihydro-2,6-dimethyl-3-nitropyridine-5-carboxylate (diastereomer B)

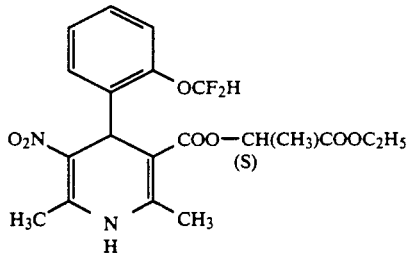

Melting point: 125°-126° C.

EXAMPLE 35

2-Phenoxyethyl 4-(2-difluoromethoxyphenyl)-1,4-dihydro-2,6-dimethyl-3-nitropyridine-5-carboxylate

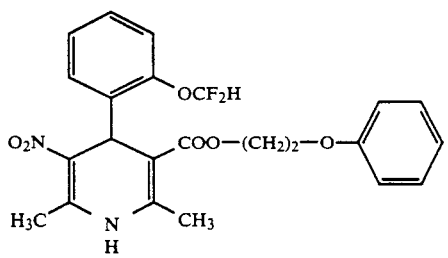

Melting point: 160°-162° C.

EXAMPLE 36

2-tert.-Butoxycarbonylamino-2-phenyl-ethyl 4-(2-difluoromethoxyphenyl)-1,4-dihydro-2,6-dimethyl-3-nitropyridine-5-carboxylate

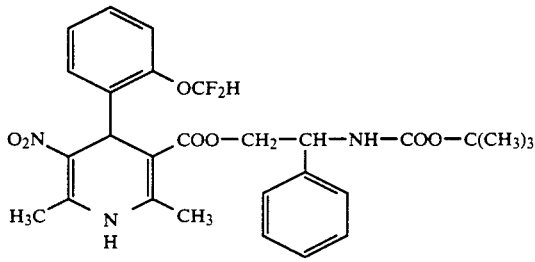

Melting point: 115°-119° C.

EXAMPLE 37

(1,1-Dimethyl-2-phenyl)ethyl 4-(2-difluoromethoxyphenyl)-1,4-dihydro-2,6-dimethyl-3-nitropyridine-5-carboxylate

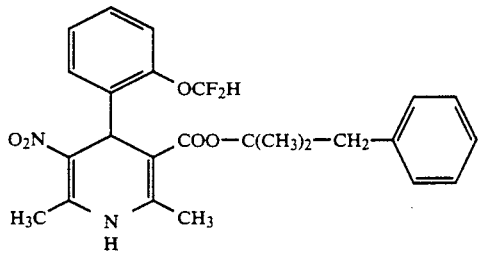

Melting point: 140°-141° C.

EXAMPLE 38

2-tert.-Butoxycarbonylamino-4-methylpentyl 4-(2-difluoromethoxyphenyl)-1,4-dihydro-2,6-dimethyl-3-nitropyridine-5-carboxylate

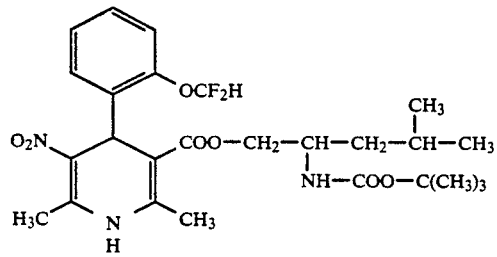

Melting point: 160°-162° C.

EXAMPLE 39

Benzyl 4-(2-difluoromethoxyphenyl)-1,4-dihydro-2,6-dimethyl-3-nitropyridine-5-carboxylate

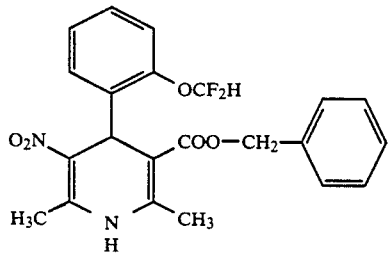

Melting point: 120°-122° C.

EXAMPLE 40

1-Phenethyl 4-(2-difluoromethoxyphenyl)-1,4-dihydro-2,6-dimethyl-3-nitropyridine-5-carboxylate

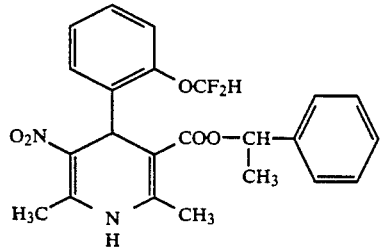

Melting point: 165°-169° C.

EXAMPLE 41

2-Picolyl 4-(2-difluoromethoxyphenyl)-1,4-dihydro-2,6-dimethyl-3-nitropyridine-5-carboxylate

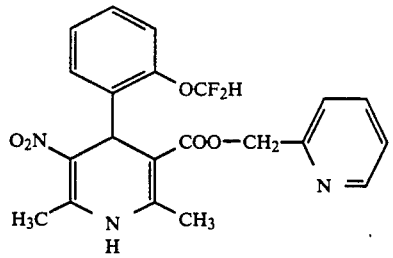

Melting point: 178°-180° C.

EXAMPLE 42

Cyclopropylmethyl 4-(2-difluoromethoxyphenyl)-1,4-dihydro-2,6-dimethyl-3-nitropyridine-5-carboxylate

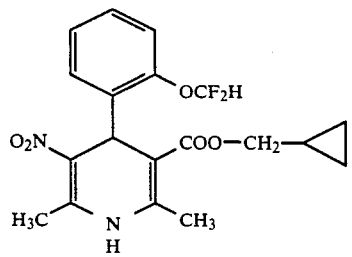

Melting point: 134°-136° C.

EXAMPLE 43

2-tert.-Butoxycarbonylamino-3-phenyl-propyl 4-(2-difluoromethoxyphenyl)-1,4-dihydro-2,6-dimethyl-3-nitropyridine-5-carboxylate

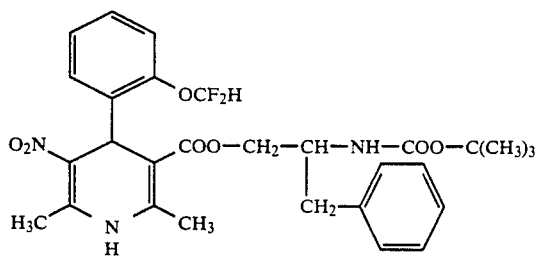

Melting point: 193° C.

EXAMPLE 44

1-(S)-(1-Isopropoxycarbonylethyl) 4-(2-difluoromethoxyphenyl)-1,4-dihydro-2,6-dimethyl-3-nitropyridine-5-carboxylate (diastereomer B)

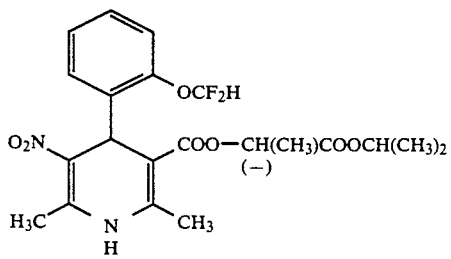

Melting point: 96°-98° C.

EXAMPLE 45

(α-Methoxycarbonyl-1-phenyl)methyl 4-(2-difluoromethoxyphenyl)-1,4-dihydro-2,6-dimethyl-3-nitropyridine-5-carboxylate (diastereomer A)

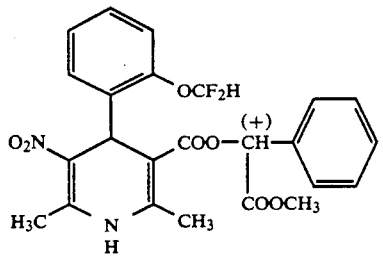

$R_f$=0.63 (methylene chloride:ethyl acetate 10:1)

EXAMPLE 46

(α-Methoxycarbonyl-1-phenyl)methyl 4-(2-difluoromethoxyphenyl)-1,4-dihydro-2,6-dimethyl-3-nitropyridine-5-carboxylate (diastereomer B)

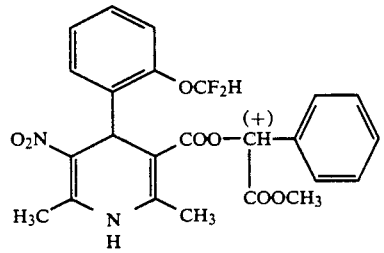

$R_f$=0.55 (methylene chloride:ethyl acetate 10:1)

EXAMPLE 47

(α-Methoxycarbonyl-1-phenyl)methyl 4-(2-difluoromethoxyphenyl)-1,4-dihydro-2,6-dimethyl-3-nitropyridine-5-carboxylate (diastereomer A)

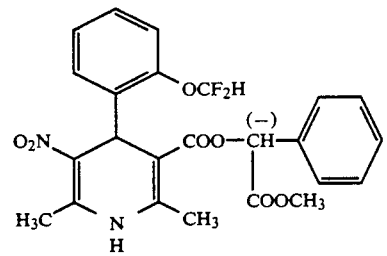

$R_f$=0.63 (methylene chloride:ethyl acetate 10:1)

EXAMPLE 48

(α-Methoxycarbonyl-1-phenyl)methyl 4-(2-difluoromethoxyphenyl)-1,4-dihydro-2,6-dimethyl-3-nitropyridine-5-carboxylate (diastereomer B)

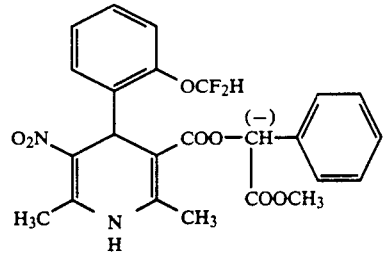

$R_f$=0.55 (methylene chloride:ethyl acetate 10:1)

EXAMPLE 49

Allyl 4-(2-difluoromethoxyphenyl)-1,4-dihydro-2,6-dimethyl-3-nitropyridine-5-carboxylate

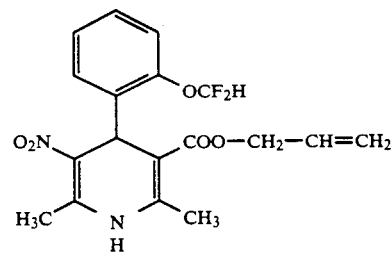

Melting point: 135°–137° C.

EXAMPLE 50

Cyclopentyl 4-(2-difluoromethoxyphenyl)-1,4-dihydro-2,6-dimethyl-3-nitropyridine-5-carboxylate

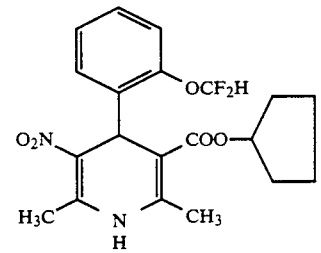

Melting point: 134°–136° C.

EXAMPLE 51

Cyclohexylmethyl 4-(2-difluoromethoxyphenyl)-1,4-dihydro-2,6-dimethyl-3-nitropyridine-5-carboxylate

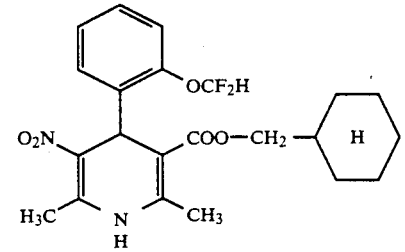

$R_f$=0.68 (toluene:ethyl acetate 1:1)

EXAMPLE 52

Cyclohexyl 4-(2-difluoromethoxyphenyl)-1,4-dihydro-2,6-dimethyl-3-nitropyridine-5-carboxylate

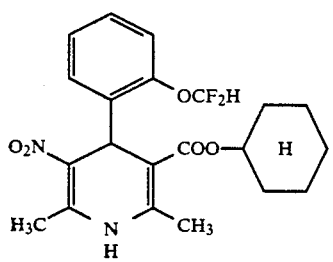

Melting point: 171°-173° C.

EXAMPLE 53

Methallyl 4-(2-difluoromethoxyphenyl)-1,4-dihydro-2,6-dimethyl-3-nitropyridine-5-carboxylate

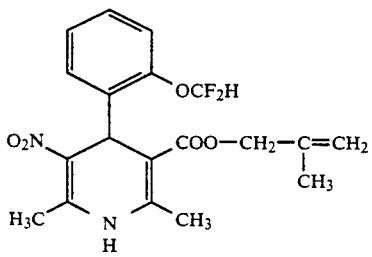

Melting point: 98°-100° C.

EXAMPLE 54

(2-Methoxy-2-phenyl)ethyl 4-(2-difluoromethoxyphenyl)-1,4-dihydro-2,6-dimethyl-3-nitropyridine-5-carboxylate (diastereomer mixture)

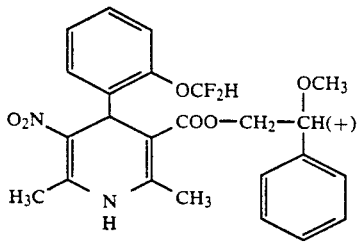

EXAMPLE 55

Octyl 4-(2-difluoromethoxyphenyl)-1,4-dihydro-2,6-dimethyl-3-nitropyridine-5-carboxylate ((−)-enantiomer)

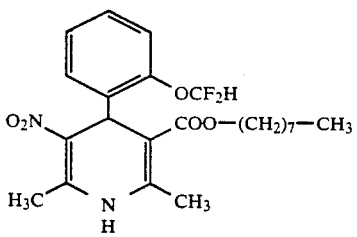

Melting point: $[\alpha]_{589}^{20} = -26.65$ (c=1.076, chloroform)

EXAMPLE 56

2-Phenethyl 4-(2-difluoromethoxyphenyl)-1,4-dihydro-2,6-dimethyl-3-nitropyridine-5-carboxylate ((−)-enantiomer)

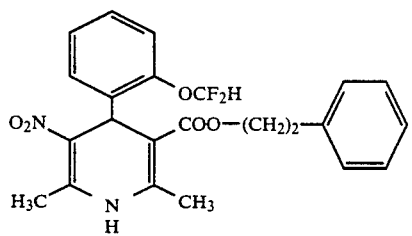

Melting point: 147°-149° C.

EXAMPLE 57

Benzyl 4-(2-difluoromethoxyphenyl)-1,4-dihydro-2,6-dimethyl-3-nitropyridine-5-carboxylate ((−)-enantiomer)

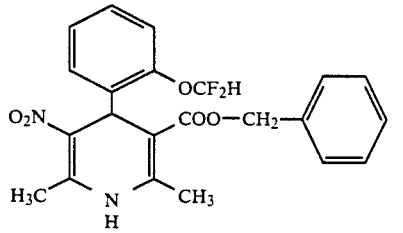

$R_f$=0.51 (toluene/ethyl acetate 2:1)
Melting point: $[\alpha]_{589}^{20} = 49.9$ (chloroform)

EXAMPLE 58 (analogous to Examples 1-3)

10-Hydroxydecyl 4-(2-difluoromethoxyphenyl-1,4-dihydro-2,6-dimethyl-3-nitropyridine-5-carboxylate

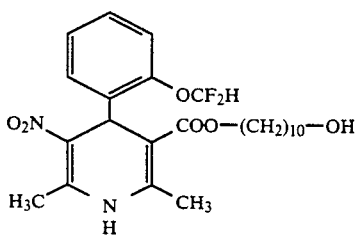

Melting point: 98° C.

EXAMPLE 59

10-Hydroxydecyl 4-(2-difluoromethoxyphenyl-1,4-dihydro-2,6-dimethyl-3-nitropyridine-5-carboxylate

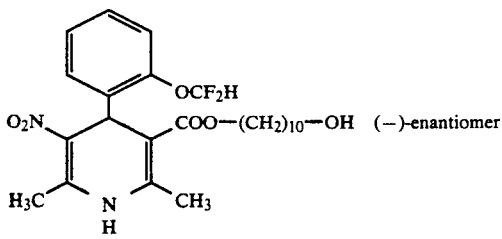

[α]₅₈₉²⁰ = −27.92 (chloroform)
Melting point: 123° C.

EXAMPLE 60

Heptyl 4-(2-trifluoromethoxyphenyl)-1,4-dihydro-2,6-dimethyl-3-nitropyridine-5-carboxylate

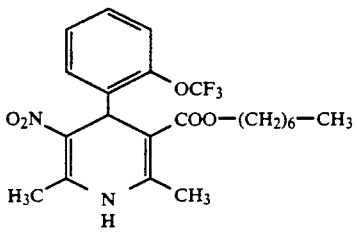

EXAMPLE 61

Octyl 4-(2-trifluoromethoxyphenyl)-1,4-dihydro-2,6-dimethyl-3-nitropyridine-5-carboxylate

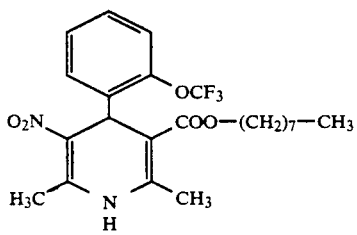

10.65 g (50 mmol) of octyl β-aminocrotonate, 9 g (87.5 mmol) of nitroacetone and 3 ml (50 mmol) of acetic acid are added to 9.5 g (50 mmol) of 2-trifluoromethoxybenzaldehyde in 75 ml of ethanol and the mixture is boiled for 4 hours. It is then cooled and concentrated. The oily evaporation residue is taken up in ethyl acetate, washed with water, sodium hydrogen carbonate solution and again with water, dried and concentrated. The oil obtained is purified over a 600 ml silica gel column using toluene/ethyl acetate. The clean fractions are combined, concentrated and crystallized using ether. The crystals are filtered off with suction and washed with ether. 6.7 g (28.5% of theory) of yellow crystals of melting point 120°-122° C. are obtained.

EXAMPLE 62 n-Butyl 1,4-dihydro-2,6-dimethyl-3-nitro-4-(2-trifluoromethoxyphenyl)-pyridine-5-carboxylate

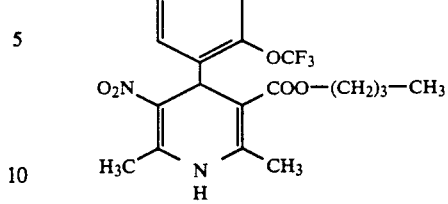

20 mmol = 2.75 g of 2-trifluoromethoxybenzylidenenitroacetone in 15 ml of ethanol are boiled for 4 hours with 10 mmol = 1.53 g of n-butyl β-aminocrotonate and 0.6 mmol of glacial acetic acid. The mixture is cooled and concentrated. The evaporation residue is taken up in ethyl acetate, washed with water, sodium hydrogen carbonate solution and water again, dried and concentrated. The oil obtained is purified over a silica gel column using toluene/ethyl acetate mixtures. The clean fractions are concentrated, and the evaporation residue is crystallized using hexane/ether, filtered off with suction and washed with hexane. 3.2 g (77.3% of theory) of yellow crystals of melting point 122° C. are obtained.

The following are prepared analogously to Examples 64 and 65:

EXAMPLE 63 n-Dodecyl 4-(2-trifluoromethoxyphenyl)-1,4-dihydro-2,6-dimethyl-3-nitropyridine-5-carboxylate

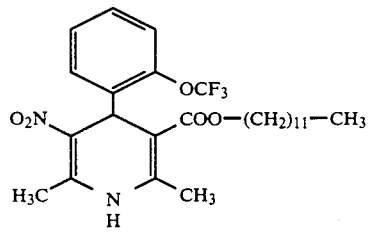

Melting point: 109° C.

EXAMPLE 64

2-(2-Pyridyl)ethyl 4-(2-trifluoromethoxyphenyl)-1,4-dihydro-2,6-dimethyl-3-nitropyridine-5-carboxylate

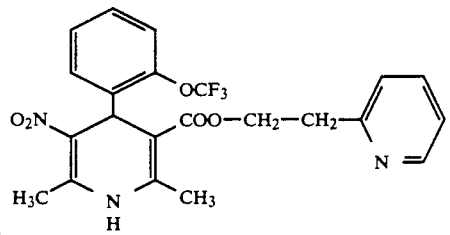

Melting point: 170° C.

EXAMPLE 65

3,3-Dimethylbutyl 4-(2-trifluoromethoxyphenyl)-1,4-dihydro-2,6-dimethyl-3-nitropyridine-5-carboxylate

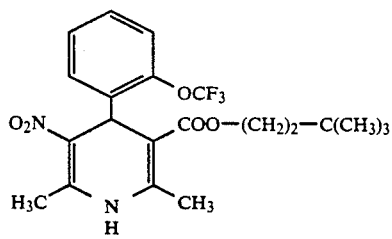

Melting point: 112° C.

EXAMPLE 66

2-Acetoxyethyl 4-(2-trifluoromethoxyphenyl)-1,4-dihydro-2,6-dimethyl-3-nitropyridine-5-carboxylate

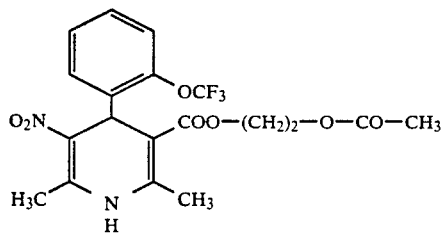

Melting point: 113° C.

EXAMPLE 67

Isopropyl 4-(2-trifluoromethoxyphenyl)-1,4-dihydro-2,6-dimethyl-3-nitropyridine-5-carboxylate

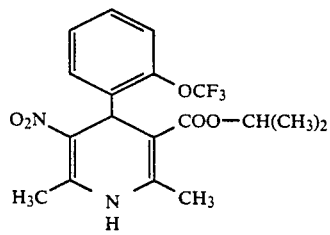

Melting point: resin

EXAMPLE 68

2-Cyanoethyl 4-(2-trifluoromethoxyphenyl)-1,4-dihydro-2,6-dimethyl-3-nitropyridine-5-carboxylate

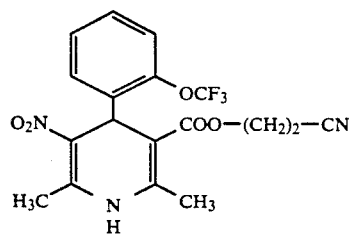

Melting point: resin

EXAMPLE 69

2-(N-Benzyl-N-methylamino)ethyl 4-(2-trifluoromethoxyphenyl)-1,4-dihydro-2,6-dimethyl-3-nitropyridine-5-carboxylate

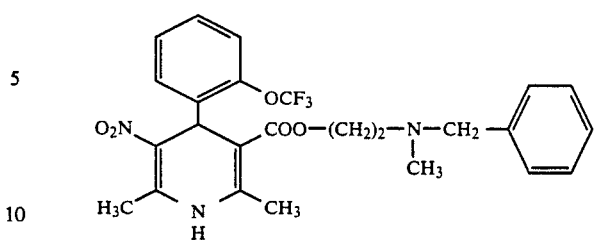

Melting point: resin

EXAMPLE 70

2-(N-Piperidinyl)ethyl 4-(2-trifluoromethoxyphenyl)-1,4-dihydro-2,6-dimethyl-3-nitropyridine-5-carboxylate

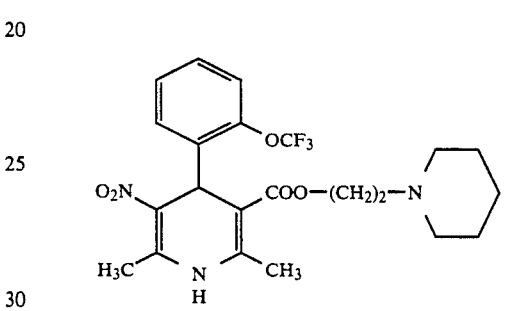

Melting point: 150° C.

EXAMPLE 71

Nonyl 4-(2-trifluoromethoxyphenyl)-1,4-dihydro-2,6-dimethyl-3-nitropyridine-5-carboxylate

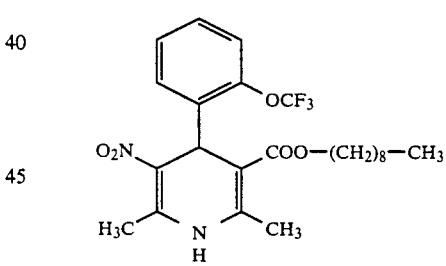

EXAMPLE 72

Hexadien-2,4-yl 4-(2-difluoromethoxyphenyl)-1,4-dihydro-2,6-dimethyl-3-nitropyridine-5-carboxylate ((−)-enantiomer)

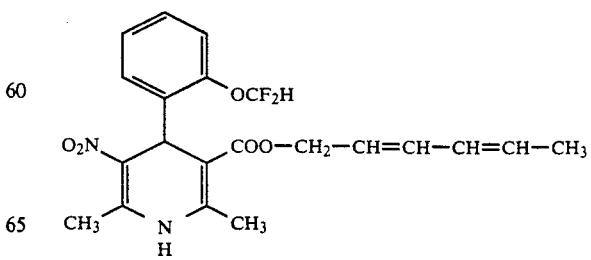

Melting point: 162° C.

EXAMPLE 73

Cinnamyl 4-(2-difluoromethoxyphenyl)-2,4-dihydro-2,6-dimethyl-3-nitropyridine-5-carboxylate ((−)-enantiomer)

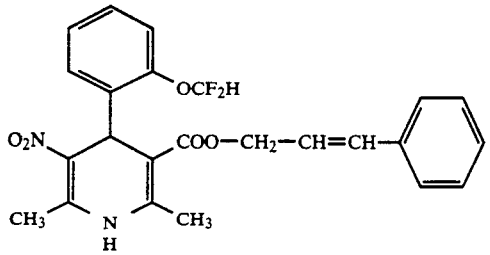

Melting point: 218° C.

EXAMPLE 74

2-(N-Benzyl-N-methyl)aminoethyl 4-(2-difluoromethoxyphenyl)-1,4-dihydro-2,6-dimethyl-3-nitropyridine-5-carboxylate ((−)-enantiomer)

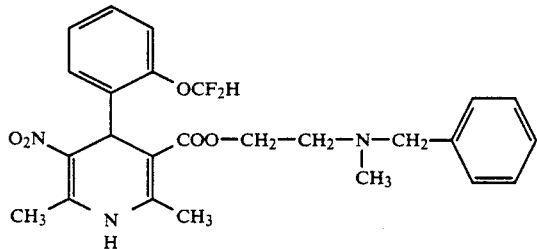

Melting point: 109° C.

EXAMPLE 75

2-(N-Benzyl)aminoethyl 4-(2-difluoromethoxyphenyl)-1,4-dihydro-2,6-dimethyl-3-nitropyridine-5-carboxylate ((−)-enantiomer)

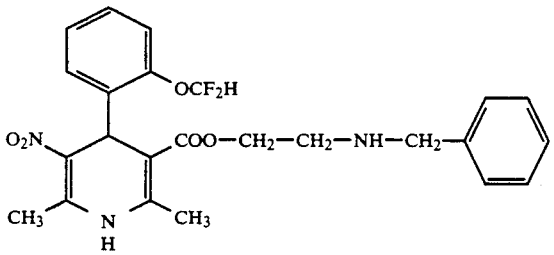

Melting point: 141° C.

EXAMPLE 76

1,1-Diethyl-methyl-4-(2-difluoromethoxyphenyl)-1,4-dihydro-2,6-dimethyl-3-nitropyridine-5-carboxylate

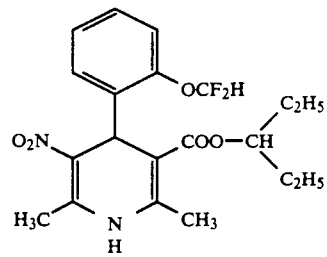

melting point: oil

It will be appreciated that the instant specification and claims are set forth by way of illustration and not limitation, and that various modifications and changes may be made without departing from the spirit and scope of the present invention.

What is claimed is:

1. A fluoromethoxyphenyldihydropyridine of the formula

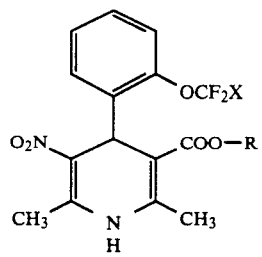

in which

X stands for hydrogen or fluorine and

R stands for straight-chain or branched alkyl or alkenyl having 2 to 12 carbon atoms which can be interrupted by 1 to 2 oxygen and/or sulphur atoms in the chain or for cyclic alkyl or alkenyl having up to 12 carbon atoms, which alkyl, alkenyl, cyclic alkyl or cyclic alkenyl radical can be monosubstituted or polysubstituted (a) by hydroxyl, aryl having 6 to 12 carbon atoms, aryloxy having 6 to 12 carbon atoms, where the aryl radical is again substituted by alkyl having up to 4 carbon atoms, alkoxy having up to 4 carbon atoms or halogen, the substituents being identical or different, or (b) by carboxyl, alkoxycarbonyl having up to 6 carbon atoms, pyridyl, piperidyl, pyrimidyl, acyloxy having up to 7 carbon atoms, sulphamoyl, carbamoyl, halogen or cyano, the substituents being identical or different, or (c) by an amino group, where the amino group can carry one or two identical or different substituents from the group consisting of alkyl having up to 6 carbon atoms, benzyl, phenyl or acyl having up to 7 carbon atoms, or a salt thereof.

2. A compound or salt according to claim 1, in which R stands for straight-chain or branched alkyl having 2 to 12 carbon atoms, which can be interrupted by oxygen and/or sulphur atoms in the chain, or for cyclic alkyl or alkenyl having up to 12 carbon atoms, which alkyl, alkenyl, cyclic alkyl or cyclic alkenyl radical can be monosubstituted or disubstituted by hydroxyl, cyano, phenyl, by phenoxy which is optionally substituted by methoxy, methyl, fluorine or chlorine, by alkoxycarbonyl having up to 6 carbon atoms, by pyridyl, piperidyl, acetoxy, benzoyloxy or by an amino group, where the amino group can carry one or two identical or different substituents form the group consisting of alkyl having up to 4 carbon atoms, benzyl or acetyl, or for straight-chain or branched alkenyl having up to 10 carbon atoms.

3. A compound or salt according to claim 1, in which R stands for straight-chain or branched alkyl having 2 to 12 carbon atoms which can be interrupted by an oxygen atom or a sulphur atom in the chain and which can be monosubstituted or disubstituted by hydroxyl, cyano, phenyl, phenoxy, 4-methoxyphenoxy, pyridyl, alkoxycarbonyl having up to 4 carbon atoms, amino or benzylmethylamino, the substituents being identical or different, or for straight-chain or branched alkenyl having up to 10 carbon atoms, or for cyclopropyl, cyclopentyl, cyclohexyl, cyclopropylmethyl, cyclopentylmethyl or cyclohexylmethyl.

4. A compound according to claim 1, wherein such compound is 2-(N-benzyl-N-methyl)aminoethyl 4-(2-difluoromethoxyphenyl)-1,4-dihydro-3-nitropyridine-5-carboxylate of the formula

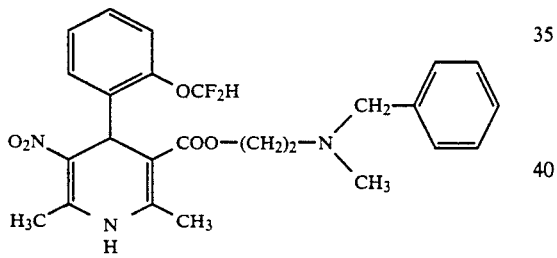

or a salt thereof.

5. A compound according to claim 1, wherein such compound is octyl 4-(2-difluoromethoxyphenyl)-1,4-dihydro-2,6-dimethyl-3-nitropyridine-5-carboxylate of the formula

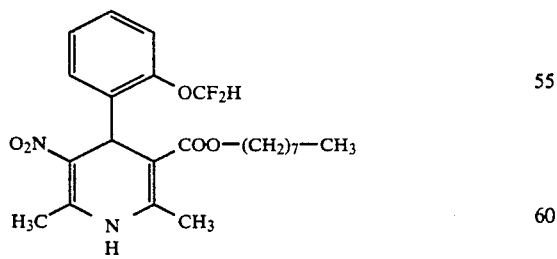

or a salt thereof.

6. A compound according to claim 1, wherein such compound is 2-(4-methoxyphenoxy)ethyl 4-(2-difluoromethoxyphenyl)-1,4-dihydro-2,6-dimethyl-3-nitropyridine-5-carboxylate of the formula

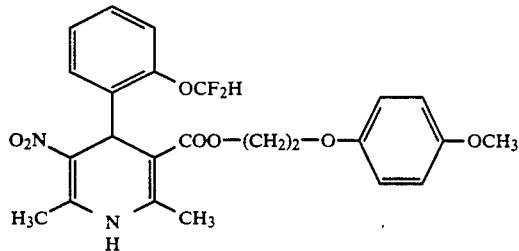

or a salt thereof.

7. A compound according to claim 1, wherein such compound is the enantiomer octyl 4-(2-difluoromethoxyphenyl)-1,4-dihydro-2,6-dimethyl-3-nitropyridine-5-carboxylate of the formula

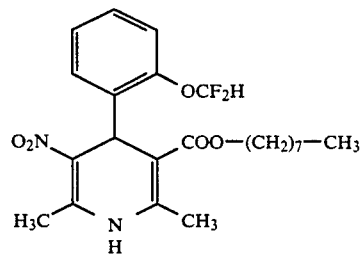

or a salt thereof.

8. A compound according to claim 1, wherein such compound is 2-phenethyl 4-(2-difluoromethoxyphenyl)-1,4-dihydro-2,6-dimethyl-3-nitropyridine-5-carboxylate of the formula

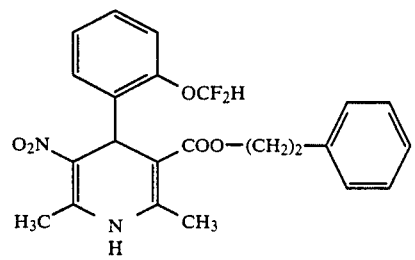

or a salt thereof.

9. A compound according to claim 1, wherein such compound is benzyl 4-(2-difluoromethoxyphenyl)-1,4-dihydro-2,6-dimethyl-3-nitropyridine-5-carboxylate of the formula

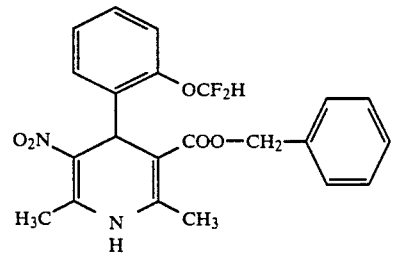

or a salt thereof.

10. A circulation-active composition comprising a circulation-active effective amount of a compound or salt according to claim 1 and a diluent.

11. A unit dose of a composition according to claim 1 in the form of a tablet, capsule or ampule.

12. A method of improving the circulation of a patient in need thereof which comprises administering to such patient a circulation-active effective amount of a compound or salt according to claim 10.

13. The method according to claim 12 wherein such compound is 2-(N-benzyl-N-methyl)aminoethyl 4-(2-difluoromethoxyphenyl)-1,4-dihydro-3-nitropyridine-5-carboxylate, octyl 4-(2-difluoromethoxyphenyl)-1,4-dihydro-2,6-dimethyl-3-nitropyridine-5-carboxylate, 2-(4-methoxyphenoxy)ethyl 4-(2-difluoromethoxyphenyl)-1,4-dihydro-2,6-dimethyl-3-nitropyridine-5-carboxylate, ethyl 4-(2-difluoromethoxypheny)-1,4-dihydro-2,6-dimethyl-3-nitropyridine-5-carboxylate, 2-phenethyl 4-(2-difluoromethoxyphenyl)-1,4-dihydro-2,6-dimethyl-3-nitropyridine-5-carboxylate, or benzyl 4-(2-difluoromethoxyphenyl)-1,4-dihydro-2,6,-dimethyl-3-nitropyridine-5-carboxylate, or a salt thereof.

14. A compound of the formula

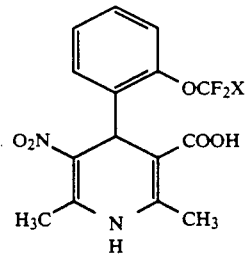

(VI)

in which

X-stands for hydrogen or fluorine.

15. A compound according to claim 1, wherein such compound is ethyl 4-(2-difluoromethoxyphenyl)-1,4-dihydro-2, 6-dimethyl-3-nitropyridine-5-carboxylate of the formula

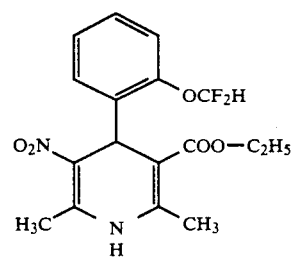

or a salt thereof.

* * * * *